United States Patent [19]
Cohen

[11] Patent Number: 5,350,297
[45] Date of Patent: Sep. 27, 1994

[54] METHOD AND APPARATUS FOR RECORDING THE POSITION OF DENTAL IMPLANTS

[76] Inventor: Robert N. Cohen, 196 Fox Tail Rd., Burlington, Mass. 01803

[21] Appl. No.: 814,402

[22] Filed: Dec. 24, 1991

[51] Int. Cl.⁵ ............................................. A61C 3/02
[52] U.S. Cl. .................................... 433/76; 433/173
[58] Field of Search ................... 433/72, 75, 76, 173, 433/172; 33/513, 514

[56] References Cited

U.S. PATENT DOCUMENTS

| | | | |
|---|---|---|---|
| 4,998,881 | 3/1991 | Lauks | 433/76 |
| 5,015,183 | 5/1991 | Fenick | 433/76 |
| 5,015,186 | 5/1991 | Detsch | 433/173 |
| 5,133,660 | 7/1992 | Fenick | 433/76 |

*Primary Examiner*—John J. Wilson
*Attorney, Agent, or Firm*—Wolf, Greenfield & Sacks

[57] ABSTRACT

A method and device for recording the position of implants secured in bone in an area having fixed surface features. The device and method feature a stent and an indexing assembly. The stent and indexing assembly record the position of the implant with respect to the surface features, which implants can later be exposed with a guided tissue punch.

11 Claims, 6 Drawing Sheets

METHOD AND APPARATUS FOR RECORDING THE POSITION OF DENTAL IMPLANTS

SUMMARY OF THE INVENTION

The present invention features methods and apparatus for recording the position of a dental implant secured to a bone in an area of a patient's mouth having surface features. In particular, the present method and apparatus feature a stent, an indexing assembly, and a tissue punch.

BACKGROUND OF THE INVENTION

The method and apparatus of the present invention are useful for aiding restorative dentists and oral surgeons in the making of teeth prostheses.

To facilitate an understanding of the present invention, a brief overview of dental implant techniques may be useful. The overview is intended to be general in nature and cannot attempt to describe all the complexities of the art and science of dentistry and oral medicine.

As used herein, the terms apical and occlusal denote positions with respect to features of a patient's teeth. Apical suggests towards the root and occlusal suggests toward the chewing and biting surfaces of the teeth.

The terms "linqual" and "buccal" also denote positions with respect to the patient's teeth. Linqual denotes toward the tongue. Buccal denotes towards the cheek.

It is the practice of the resotrative dentists and oral surgeons to make a first impression of the surface features of an area in which a dental implant is to be placed. The impression is used to make a first cast. The first cast records the surface features in a form which the dentist or surgeon can readily plan future surgery, plan the placement of abutments and the type of tooth prosthesis.

Dental implantations are performed in stages. In the first stage, surgery would be performed to expose the bone, drill a cavity in the bone, and position an implant in the cavity. Implants are available in a variety of shapes and sizes.

Generally, implants are cylindrical in form having a circular occlusal surface. The occlusal surface will normally have a threaded opening to receive a screw for securing an abutment, or to receive an abutment having a corresponding threaded section. The abutment will be fitted at a later stage. A screw is normally placed in the hole as a cap during the healing process.

To facilitate securing the implant into bone and to provide alignment surfaces for abutments to be placed on the implant, some implants have keyed occlusal surfaces. On such keyed surface commonly used is a hexagonal extension of the implant.

The oral surgeon completes the first stage of surgery by closing the open surgical wound with stitches and the like, over the implant. The oral surgeon may note the location of the implant on the first cast.

Normally, the patient will not revisit the oral surgeon for three to six months. Three to six months are required for healing, to allow the implant to be securely received in the bone tissue. During the time in which the bone is receiving the implant, the original incisions in the soft tissue are healing, obscuring the location of the implant.

Three to six months after the first stage surgery, in the second stage of surgery, the oral surgeon will expose the implant to mount a temporary healing abutment. The temporary healing abutment brings the restorative surface to the crest of the gum to facilitate tissue healing. The oral surgeon may use the first cast to facilitate locating the implant. However, the exact position of the implant, its alignment, angle and position on the horizontal and vertical axis cannot be accurately placed on the surface features of the cast.

Upon completion of the second stage of surgery, the oral surgeon will secure the soft tissue with stitches, if necessary, and gauze. Oral surgeons rarely construct prosthetic teeth beyond the placement of the abutment. Typically, the oral surgeon will refer the patient to a restorative dentist.

A patient waits ten to fourteen days for healing following the placement of the temporary healing abutment to visit the restorative dentist for the first time. The patient will likely visit the restorative dentist four times.

During the patient's first visit, the restorative dentist will evaluate whether the abutment placed by the oral surgeon is suitable for a permanent prosthesis. The restorative dentist will remove the temporary healing abutment and place an impression coping on the implant. The impression coping has a cylindrical shape and is capable of being received on the implant by screws and the like. With the impression coping in place, the restorative dentist will make an impression of the surface features and the impression coping.

The impression coping is then removed from the implant. A cast of the impression is made with the impression coping and an implant analog fitted to the impression.

During the same first visit, the restorative dentist may fit a temporary crown, bridge, or tooth of acrylic material to protect the area of the future permanent prosthesis and to provide a better cosmetic appearance for the patient.

After the patient's first visit, the restorative dentist will make a diagnostic cast from the final impression. The restorative dentist will secure an implant analog to the impression coping. With the impression coping carried in the hole created when the impression was made, plaster will be poured into the impression. The diagnostic cast gives the location of the abutment or implant within the context of the surface features of the patient's mouth.

With the diagnostic cast, the restorative dentist will make a permanent abutment selection. The permanent abutment is ordered for placement in the patient's mouth at the next visit.

At the second visit, the restorative dentist secures the permanent abutment to the implant. The restorative dentist will confirm by X-ray that the permanent abutment is seated. The restorative dentist will also make a final impression.

The final impression is made with a further impression coping secured to the abutment. From the final impression, a final cast is made. An impression coping secured to an abutment analog is fitted to the impression and plaster poured into the final impression to form the final cast. The impression coping is removed to reveal an abutment analog secured in the final cast in the same respective position as the abutment in the patient's mouth.

The final cast is most often made in a dental laboratory from the final impression. With the final cast as a guide, the dental laboratory will fabricate a tooth prosthesis.

The tooth prosthesis is sent to the restorative dentist. At a third visit, the restorative dentist will temporarily mount the tooth prosthesis to the abutment to insure the tooth prosthesis fits with other teeth and features of the patient's mouth. The tooth prosthesis is then returned to the dental lab to be completed. After the dental laboratory completes the tooth prosthesis, it is sent back to the restorative dentist. The patient returns to the restorative dentist and the tooth prosthesis is permanently mounted to the abutment. The entire process of replacing a tooth may take nine months.

The long nine month period and repeated visits to the oral surgeon and the restorative dentist discourages patients from engaging in implant dentistry. Each visit to the oral surgeon and restorative dentist may produce uncomfortable experiences for patients, and increases the opportunities for patients to reevaluate their interest in having a tooth prosthesis.

A shorter period of time between the initiation of oral surgery and the fitting of a final tooth prosthesis would be more convenient, shorten periods of discomfort and provide improved cosmetic appearance and dental function for the patient. A reduction in the number of visits to oral surgeons and restorative dentists may reduce the cost of restorative dentistry.

BRIEF DESCRIPTION OF THE INVENTION

The present invention features a method and device for recording the position of a dental implant with respect to surface features in a patient's mouth. Such surface features may include other teeth, implants or other substantially immovable surfaces capable of being located at a later time.

One embodiment of the present invention features a device for recording the position of a dental implant secured to a bone in an area having surface features. The device comprises a stent, which stent has an elongated member having a spanning section and at least one receiving surface. The receiving surface is capable of receiving and permanently conforming to at least one surface feature. The spanning section is adapted to extend to a position adjacent the implant. The device further comprises an indexing assembly. The index assembly is capable of being secured to the spanning section and is releasibly secured to the implant, recording the position of the implant with respect to the surface feature in the position of the index assembly secured to the stent. The stent is removed from surface feature and the index assembly is released from the implant. The stent can be positioned on a cast of the surface features or placed into a patient's mouth at a later time to identify the placement of the implant.

One embodiment of the present device features an index assembly comprising an implant coping and an index coping. The implant coping is adapted to be secured to the implant. The index coping is adapted to be secured to the spanning section of the stent.

The implant coping has an apical section and an occlusal section. The apical section has a cylindrical shape with a circular apical surface capable of being received on an implant and an implant analog. The occlusal section extends from the apical section in a frustra conical shape. One embodiment of the present invention features an occlusal section having alignment surfaces to facilitate the positioning of a dental prosthesis with respect to surface features. The apical section is adapted to be positioned below the gum tissue line. The occlusal section is adapted to extend above the gum tissue.

The index coping has substantially cylindrical shape having an apical end and an occlusal end. The apical end has a cavity capable of releasibly receiving the occlusal section of the implant coping. The occlusal end is capable of being secured to the spanning section of the stent. Preferably, the occlusal end is secured to the spanning section with acrylic adhesive.

One embodiment of the present invention features an implant coping and an index coping having cooperating openings, which cooperating openings cooperate with a threaded opening in the implant. A screw is received in the cooperating opening of the index assembly and the threaded opening of the implant. The screw maintains a proper alignment of the stent, index coping, and implant coping with respect to the implant, during the curing of the acrylic adhesive. The index coping, secured to the stent, records the position of the implant, with respect to the surface feature.

An alternative embodiment of the present invention features an implant coping having a screw section extending from the circular apical surface. The screw section is capable of being received by a cooperating threaded opening in the implant.

The alternative embodiment features an implant coping having a threaded opening capable of cooperating with an opening in the index coping and an opening in the spanning section of the stent to receive a screw.

Embodiments of the present apparatus allow an oral surgeon to make an initial cast of the patient's mouth recording surface features. The oral surgeon can place an implant within the bone tissue of the patient. The index assembly comprising the implant coping and the index coping can be fitted to the implant and the stent secured to surface features of the patient's mouth, to record the position of the implant at first stage surgery.

Later, at a dental laboratory, the stent is positioned onto the analogous surface features of a cast, which cast is drilled with the opening of the index coping and stent providing alignment of the axis of the implant. The implant coping and an implant analog are secured to the index coping as the index assembly was assembled on the implant in the mouth of the patient. The index assembly positions the implant analog in the same, spatial relationship with respect to analogous surface features, where the implant analog is permanently fixed.

The restorative dentist can make suitable abutment selections based upon the accurate positional relationship of the implant within the cast of the patient's mouth prior to the first visit, even prior to the second stage surgery.

The dental laboratory may place the abutment selected by the reconstructive dentist onto the implant analog, and proceed to construct a dental prosthesis.

At the second stage surgical visit, the oral surgeon can accurately identify the position of the dental implant with the use of the stent. Having determined the position of the implant with the stent, the dentist may quickly remove tissue from above the implant to allow an appropriate abutment to be placed thereon.

One embodiment of the present invention features a tissue punch assembly capable of working in cooperation with a stent used to place implant analogs in a cast. The stent and the tissue punch assembly are used to quickly remove the tissue from above the implant. The tissue punch assembly comprises a tissue punch, tissue punch guide and a tissue punch guide setter.

The tissue punch has a cylindrical shape having an apical end, an occlusal end, a outer diameter and an axial length. The apical end of the tissue punch has an axial opening defining a hollow cavity adapted to receive tissue. The edge of the opening defines a cutting surface for moving through soft tissue such as the gum. The occlusal end has handling means to allow the oral surgeon to manipulate the tissue punch. One embodiment features an occlusal end equipped with rubber tool handle material. A further embodiment features keyed openings adapted to cooperate with handling equipment, to allow an oral surgeon to manipulate the tissue punch.

A further embodiment of the present apparatus features an occlusal end having an axial keyed opening adapted to receive handling equipment. The handling equipment cooperating with the keyed opening allows the tissue punch to be rotated within the tissue punch guide as the tissue punch is forced through the tissue to facilitate the cutting action of the cutting edge.

The tissue punch guide setter has a cylindrical shape having a diameter and two ends. One end is adapted to be positioned towards the implant or an implant analog. The tissue punch guide setter is tapered at the end directed to the analaog to the tissue punch guide setter to readily seat against the implant. The diameter of the tissue punch guide setter is substantially equal to the diameter of the tissue punch. Preferably, the tissue punch guide setter has an opening extending radially therethrough, capable of receiving a screw. The opening of the tissue punch guide setter cooperates with an opening in the implant. The tissue punch guide setter is positioned in the same position with respect to the implant analog as the index assembly had assumed previously.

The tissue punch guide is a cylindrical sleeve having an axial length, an inside diameter, and two ends. The tissue punch guide is adapted to slidably receive the tissue punch guide setter and the tissue punch about the inside diameter. The axial length of the tissue punch guide is sized to provide adequate support as a guide surface for the tissue punch, and the tissue punch guide setter, yet provide clearance from the soft tissues apical to the stent. While the tissue punch guide setter is positioned on the implant or implant analog, the tissue punch guide is secured to the stent. Preferably the tissue punch guide is secured with an acrylic adhesive to permanently record the position of the implant or implant analog. After the tissue punch guide is permanently affixed to the stent, the tissue punch guide setter may be removed from the stent, and the implant or implant analog.

At the second stage surgery, the oral surgeon positions the stent carrying the tissue punch guide in place in the patient's mouth. The stent records the position of the implant in relation to the surface features to which the stent is received. The oral surgeon inserts the tissue punch through the tissue punch guide and works the tissue punch through the gum to the implant. With the implant exposed, the oral surgeon can mount the selected abutment.

Features of the index assembly and the tissue punch assembly can be combined. Combining aspects of the tissue punch assembly and the index assembly simplifies the use of the assemblies.

One embodiment of the present device features a tissue punch guide which is capable of slidably receiving an index assembly. The tissue punch guide is capable of releasibly securing the index assembly to the stent. The index assembly act in the manner of the tissue punch guide setter, to set the position of the tissue punch guide with respect to the implant.

One embodiment of the tissue punch guide features a pin which is received in an opening in the tissue punch guide and indexing to immobilize the two elements with respect to each other.

Thus, the index assembly is secured to the stent through the tissue punch guide. The index assembly is adapted to be released from the tissue punch guide and reassembled to allow the transfer of the respective position of the implant to a cast. The tissue punch guide is secured to the stent by suitable means such as acrylic and need not be disturbed for later applications.

Stent can be fashioned from acrylic cement. However, to fashion a stent from acrylic, takes time. One embodiment of the present invention features a registration tray. The registration tray is an elongated member corresponding generally to the occlusal surfaces of a patient's mouth.

The elongated member has at least one receiving surfaces capable of receiving and conforming to surface features of the patient's mouth. The elongated member has a spanning section capable of being positioned adjacent to the area of the patient's mouth where dental implants are to be placed.

Preferably, the spanning section is capable of assuming a position lingual to the site of the implant, to allow an oral surgeon to work at the site of the implant without interference.

One embodiment features a preformed tray. The preformed tray has a plurality of areas capable of receiving surface features and spanning sections. Areas of the tray which are capable of functioning as receiving surfaces may, for some patients, be in the position of the site for the intended implant. One embodiment of the present invention features receiving sections which can be readily removed if not needed, or if such sections overlay the site of the gum where implants are to be placed, leaving a spanning section disposed lingually of the implant site. The spanning section is adapted to receive the index assembly. One embodiment of the present invention features a tray with areas defined by scoring to facilitate removal.

One further embodiment of the present invention features a method for recording a position of a dental implant secured to a bone or tooth in an area of a patient's mouth having surface features. The method comprises the step of releasibly securing a stent to at least one surface feature. The stent comprises an elongated member having a spanning section and at least one receiving surface capable of receiving and permanently conforming to such surface feature. The spanning section is adapted to extend from the receiving surface to a position adjacent to the implant. An index assembly is secured to the stent and releasibly secured to the implant. Release of the stent from the surface features and release of the index assembly from the implant records the position of the dental implant with respect to the surface feature.

One embodiment of the present method features an indexing assembly comprising an implant coping and an index coping. The implant coping has an apical section and an occlusal section.

The apical section has a cylindrical shape which shape has an end defining an apical implant surface. The apical implant surface is capable of being received on the implant. The apical section is adapted for placement below the gum surface.

The occlusal section extends from the apical section, in a frustra conical shape. One embodiment of the present invention features an occlusal section having an alignment surface to facilitate positioning of the dental prosthesis with respect to surface features. The occlusal section is adapted to protrude above the gum line of a patient.

The index coping has a cylindrical shape having an apical index end surface and an occlusal index end surface. The apical index end surface has a cavity capable of releasibly receiving the occlusal section of the implant coping. The occlusal index end surface is capable of being secured to the spanning section of the stent.

One embodiment of the present method features the steps of securing the implant coping to the implant, securing the index coping to the spanning section, as the implant coping is received in the index coping. Preferably, the occlusal index end surface is glued by acrylic means to the spanning section, while the stent and index assembly are secured to the implant. The index coping, affixed to the stent, records the position of the implant with respect to the surface features.

One embodiment of the present method features an implant coping and the index coping which have cooperating openings which openings further cooperate with a threaded opening in the implant, to receive a screw. The screw is capable of securing the index assembly to the implant as the occlusal end of the index coping is secured by acrylic to the stent. The method comprises the step of securing the implant coping and index coping to the implant with a screw.

One embodiment of the method features an implant coping capable of being secured to the implant by a screw section extending from the circular bottom. The screw section is capable of being received by a cooperating threaded opening in the implant. The method comprises the step of securing the implant coping to the implant by receiving the screw section in the threaded opening of the implant.

An alternative embodiment of the present method features an index coping capable of being secured to the implant coping by a screw. The screw extends through an opening in the index coping into a cooperating threaded opening in the implant coping. The method comprises the step of securing the index coping to the implant coping with the screw.

The screw sections and screws serve to align the index assembly in relation to the implant and the stent. Individuals skilled in the art will readily recognize that other fastening means may be readily substituted for the screws and screw sections herein described.

The present method is particularly suitable for marking the position of the implant in a cast. One embodiment of the method includes a step of making a cast of the surface features. The stent is capable of being releasibly secured to analogous surface features of the cast to allow the position of the implant to be recorded thereon. The index coping of the index assembly affixed to the coping section, is used to record the position of the implant by drilling a pilot hole with the index coping as a guide. The pilot hole is expanded to accommodate the implant coping and an implant analog. The implant coping and implant analog are secured to the index coping. The stent with the index assembly and implant analog is secured to analogous feature of the cast. The implant analog is held in an identical position with respect to the analogous surface features and is secured within the cast.

One further embodiment of the present method features exposing an implant with a tissue punch. The tissue punch is held in axial alignment with the implant by a stent. The stent has an elongated member having a spanning section and at least one receiving surface capable of receiving a surface feature of the patient's mouth to align the spanning section such that said spanning section is adjacent to said implant. The spanning section has a tissue punch guide for engaging a tissue punch and directing the tissue punch through gum tissue to the implant.

Embodiments of the present invention reduce the number of dental appointments necessary to complete implant supported prosthetics. In addition, embodiments of the present invention enable a reconstructive dentist to quickly and accurately expose implants from under tissue. These and other features will become apparent from the drawings and the detailed description which follow, which by way of example, without limitation, describe preferred embodiments of the present invention.

DETAILED DESCRIPTION OF THE DRAWINGS

Embodiments of the present invention will be discussed with respect to a method and apparatus for recording the position of dental implants. Individuals skilled in the art will readily recognize that the method and apparatus of the present invention can be used for recording the position of any implant placed in bone which implant is later covered with soft tissue.

Figure 1:
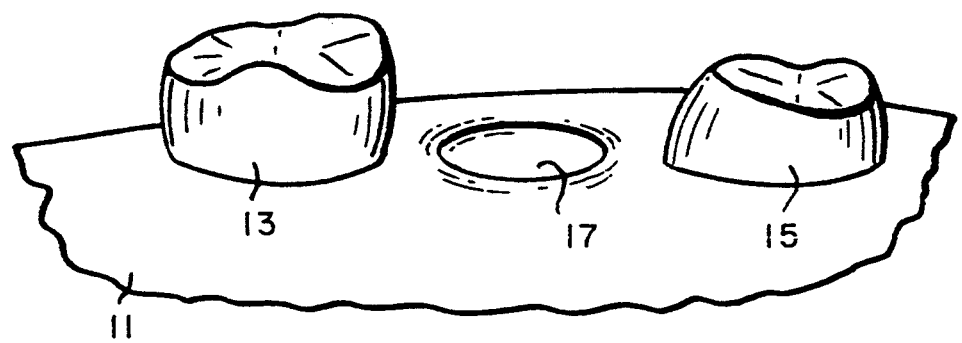
FIGS. 1 through 12 describe, sequentially, features of the present method with respect to an apparatus for recording the position of dental implants embodying features of the present invention.

Features of a mouth of a patient are illustrated in FIG. 1. The features of the patient's mouth include gum 11, a first molar 13 and a second molar 15. First molar 13 and second molar 15 are separated by a space 17 which formally was occupied by a third molar (not shown). For the purposes of the present discussion, space 17 will be the focus of restorative dentistry to build a tooth prosthesis.

The oral surgeon will make an initial impression of the surface features. The impression is used to make a cast which substantially duplicates the features in a manner readily recognized by the oral surgeon.

Figure 2:
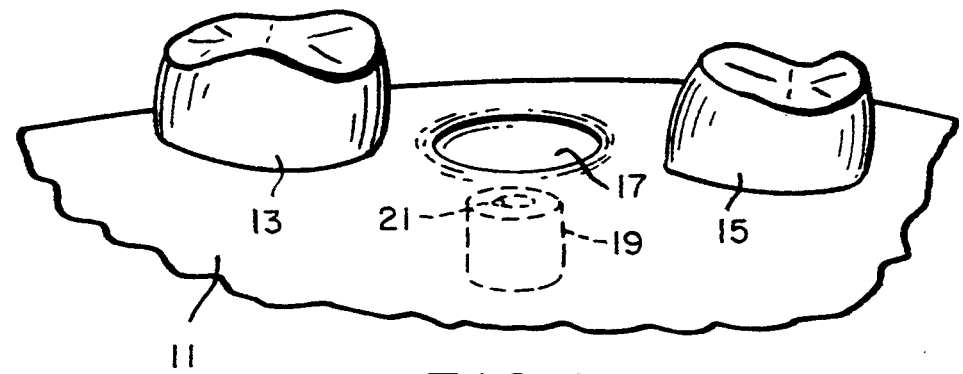

In order to build a tooth prosthesis in the space 17, the oral surgeon begins a first stage surgical procedure. The oral surgeon will surgically open the gum, drill an opening or cavity in the bone, and place an implant 19 into the bone cavity of the patient, as best illustrated in FIG. 2. The implant 19 is designed to receive bone tissue such that the implant will become permanently affixed to the bone.

The implant 19 may take several different shapes and forms. Implants 19 generally have a threaded opening 21 in which to secure an abutment. Surrounding the threaded openings 21, the implant 19 may have other alignment surfaces such as hexagonal extensions (not shown) to provide alignment of the prosthetic device to be secured to the implant and to facilitate handling the implant 19 during the surgical procedure.

Normally, the oral surgeon, after placing the implant 19, will bring the gum tissues together with a suitable closure such as sutures and the like. The bone surrounding the implant is allowed to heal over a four to six month period. During such four to six month period the soft tissue heals above the implant 19 and obscures its position.

Figure 3:
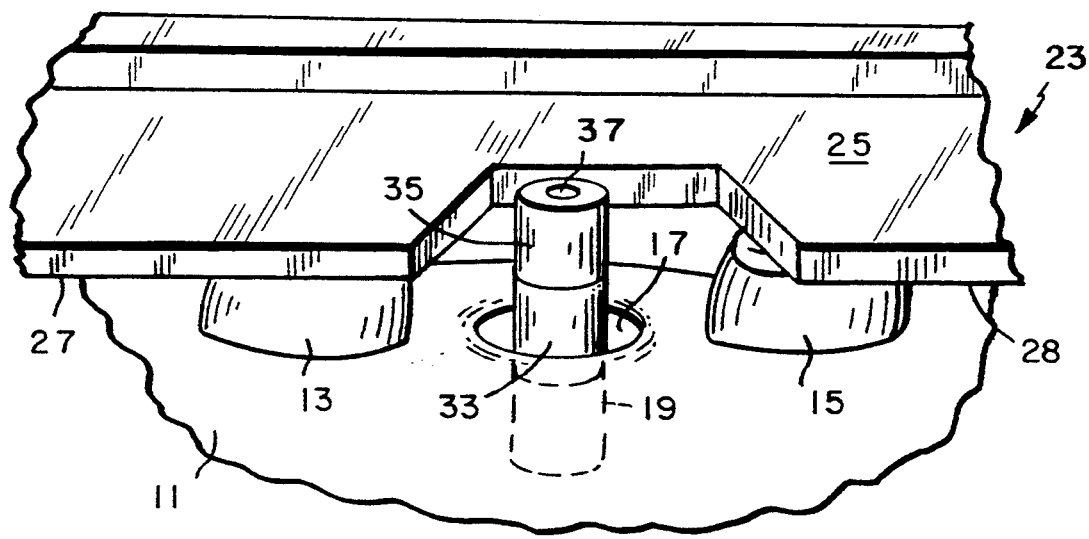

Turning now to FIG. 3, one embodiment of the present method and apparatus features a stent, generally depicted by numeral 23. The stent 23 is comprised of a substantially rigid elongated member 25 having two receiving surfaces 27 and 28 and a spanning section 29. The receiving surfaces 27 and 28 are capable of receiving and conforming to the surface features of first molar 13 and second molar 15. The spanning section 29 interposed between the receiving surfaces 27 and 28 arches lingually away from space 17 to produce clearance for manual operations, and clearance for an indexing assembly, generally designated by the numeral 31. The stent 23 is comprised of a dental grade plastic, or other suitable material.

The oral surgeon, prior to closing the opening in the patient's gum, secures an indexing assembly 31 to the implant 19 and the spanning section 29 by suitable fastening means. Three embodiments of an indexing assembly 31 are illustrated in FIGS. 13-20. The embodiments illustrated in FIGS. 17-20 will be described in greater detail towards the end of this discussion.

Figure 13:
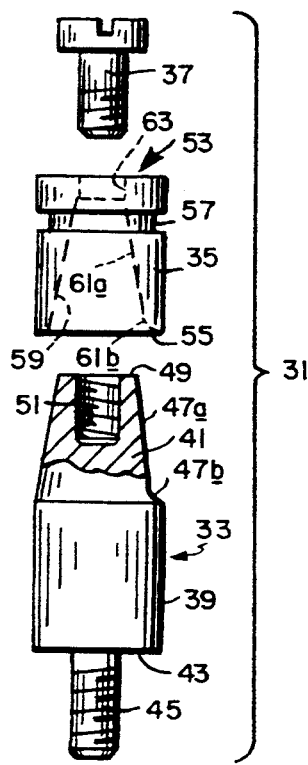
FIG. 13 depicts an indexing assembly capable of use with a stent, embodying features of the present invention.

Turning now to the embodiment illustrated in FIG. 13, the indexing assembly comprises an implant coping 33, an index coping 35 and a screw 37. The index assembly is preferably made of stainless steel or other suitable material.

The implant coping 33 has an apical section 39 and an occlusal section 41. The apical section 39 is substantially cylindrical in shape, which shape has a diameter and an apical surface 43. The diameter of the apical section 39 corresponds substantially to the cylindrical shape of the implant 19.

The diameter for implant coping 33 is approximately 4.5 mm. Total length of the implant coping 33 is approximately 11.5 mm.

A screw extension 45 extends axially from the apical surface section 43. The screw section 45 is adapted to be received within a corresponding threaded opening 21 in the implant 19 as can best be seen in FIG. 2.

Individuals skilled in the art will readily recognize that implants 19 are generally commercially available in a number of sizes and have a variety of threaded openings 21. Individuals skilled in the art will readily recognize that the implant coping 31 may be made with a plurality of a screw extensions 45 to match each threaded opening 21.

Figure 15:
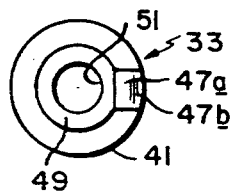
FIG. 15 depicts an apical surface of the indexing assembly of FIGS. 13 or 14.
Figure 16:
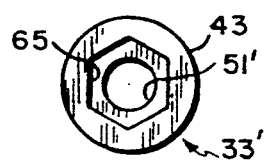
FIG. 16 illustrates the apical surface of the indexing assembly of FIG. 14.

The occlusal section 41 extends from the apical section 39. The occlusal section 41 has a generally frustra conical shape. As best seen in FIG. 15, the frustra conical shape is altered with alignment surfaces 47a and b to transfer the rotational position of the implant 19 and implant coping 33 to the index coping 35.

Returning now to FIG. 13, the occlusal section 41 has an occlusal surface 49 which is generally circular in shape which circle is interrupted by the alignment surface 47a. Occlusal surface 49 has a threaded opening 51 capable of receiving cooperating threads of screw 37.

Index coping 35 has a cylindrical shape having an occlusal end 53 and an apical end 55. The cylindrical shape has an outer diameter and a length. The diameter is selected to correspond with features of the implant coping 33. The length of the cylindrical shape is selected to allow the index coping 35 to clear surface features of the implant area 17. Index coping 35, as illustrated, has a total length of approximately 6.0 mm and an approximate outer diameter of 7.5 mm.

The occlusal end 53 is adapted to be affixed to the spanning section 29 of stent 23. A ridge 57 running around outer circumference of the index coping 35 provides a gripping surface for acrylic adhesive. The outer surface of the index coping 35 may also be machined with ribs (not shown) to facilitate the adhesion of the index coping 33 to the spanning section 29.

The apical end 55 of the index coping 35 has a cavity 59 capable of receiving the occlusal section 41 of the implant coping 33. Cavity 59 is machined to closely correspond with the features of the occlusal section 41. Cavity 59 has alignment surface 61a and 61b capable of receiving alignment surfaces 47a and 47b.

The occlusal end 53 of index coping 35 has an opening 63 capable of receiving screw 37. Opening 63 cooperates with threaded opening 51 of the implant coping 33.

Turning now to FIG. 3, screw 37 secures the index coping 35 to the implant coping 33. Implant coping 33 is secured to the implant 19 by screw extension 45 secured in a cooperating threaded opening 21 of implant 19. Index coping 35 is fastened by adhesive acrylic to the spanning section 29 of stent 23 while the index assembly 31 is held in place by screw 37 and screw extension 45.

Figure 14:
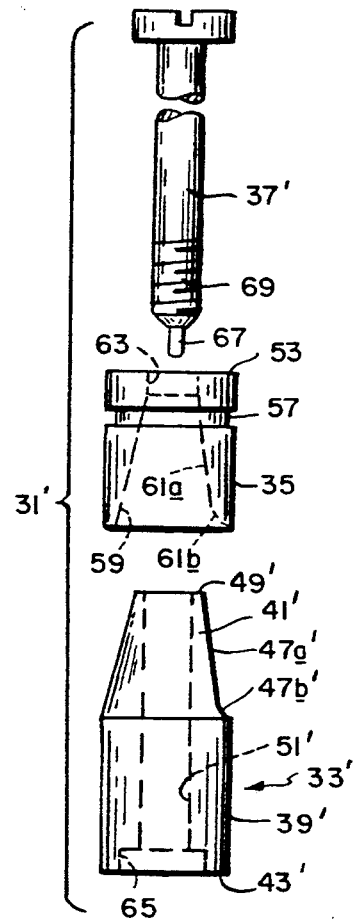
FIG. 14 illustrates an index assembly for use with a stent embodying features of the present invention.

Turning now to an alternate assembly illustrated in FIG. 14, an index assembly, generally designated by numeral 31', is comprised of an implant coping 33' and an index coping 35. The index assembly 31' depicted in FIG. 14 is used with a screw 37' capable of extending through the index coping 35 and implant coping 33 to the threaded opening 21 of implant 19.

Implant coping 33' has an apical section 39' and an occlusal section 41'. The apical section 39' has a cylindrical shape having a diameter and a circular apical surface 43'. The diameter corresponds substantially to the cylindrical shape of the implant 19. The apical surface 43' has a keyed indentation 65 as best seen in FIG. 15. The keyed indentation is capable of receiving a keyed protrusion (not shown) on implant 19.

The occlusal section 41' extends from the apical section 39'. The occlusal section 41' has a generally frustra conical shape altered with alignment surfaces 47a' and 47b' to transfer the rotational position of the implant 19 and implant coping 33' to the index coping 35.

The occlusal section 41' has an occlusal surface 49' which is generally circular in shape, which circle is interrupted by the alignment surface 47a'. Occlusal surface 49' has an opening 51' extending axially through the implant coping 33', to receive screw 37'.

The index coping 35, illustrated in FIG. 14 is identical to the index coping 35 illustrated in FIG. 13. Index coping 35 receives the occlusal section 41' of implant coping 33' within cavity 59. Opening 63 in index coping 35 cooperates with opening 51' in implant coping 33' and an opening in the spanning section 29 of stent 23, to receive screw 37'. Screw 37' is received by threaded section 69 in threaded opening 21 of implant 19. To facilitate fitting screw 37' through the openings, screw 37' has a guide projection 67 extending from threaded section 69.

In both embodiments, illustrated in FIGS. 13 and 14, the index coping 35 is glued or cemented to the spanning section 29 of stent 23 as the index assembly 31 or 31' are secured to the implant 19. For illustration purposes, the cement holding index coping 35 to the spanning section 29 has not been depicted. Suitable glue such as a dental grade acrylic cement is packed around the index coping and spanning section to create a rigid structure. Thus, the index coping 35 records the position of the implant 19 with respect to the surface features of area 17 of the implant.

Figure 4:
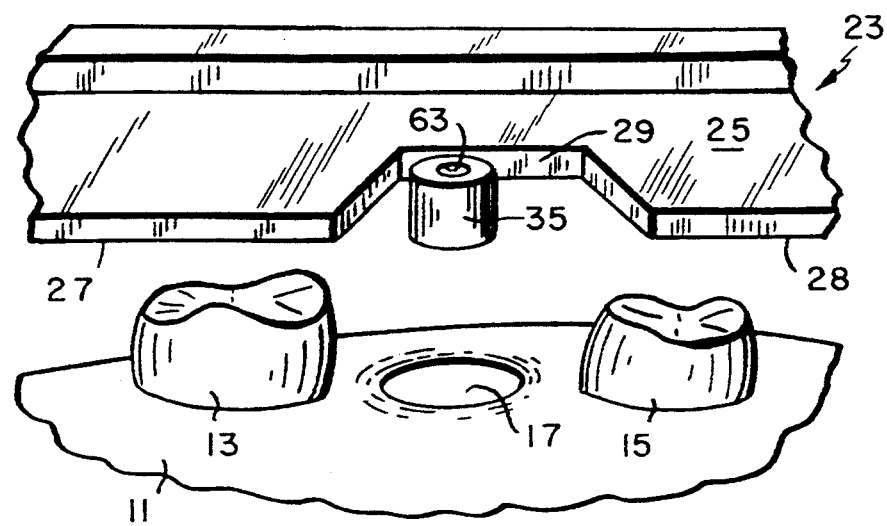

Removal of the screw 37 or 37' from the index assembly 31 or 31' allows the index coping 35 and the stent 23 to be removed as a single assemblage. With respect to the embodiment illustrated in FIG. 13, the implant coping 33 remains secured to the implant 19 by the screw extension 45 received in the threaded opening 21 of the implant 19. The oral surgeon will unscrew the implant coping 33, after removal of the stent 23 with the index coping 35, to allow the soft tissue to be secured over implant 19 as seen in FIG. 4.

With respect to the embodiment illustrated in FIG. 14, removal of the screw 37', allows the stent 23 with index coping 35 glued thereon to be removed. Implant coping 33' can also be removed to allow the soft tissue to be secured over implant 19, as illustrated in FIG. 4. Stage 1 surgery is completed at this point.

The implant 19 is allowed to heal for four to six months before any further dental or surgical procedures are performed with respect to implant 19. The stent 23, index assembly 31 and cast 73, can now be sent to a dental laboratory for further processing.

Figure 5:
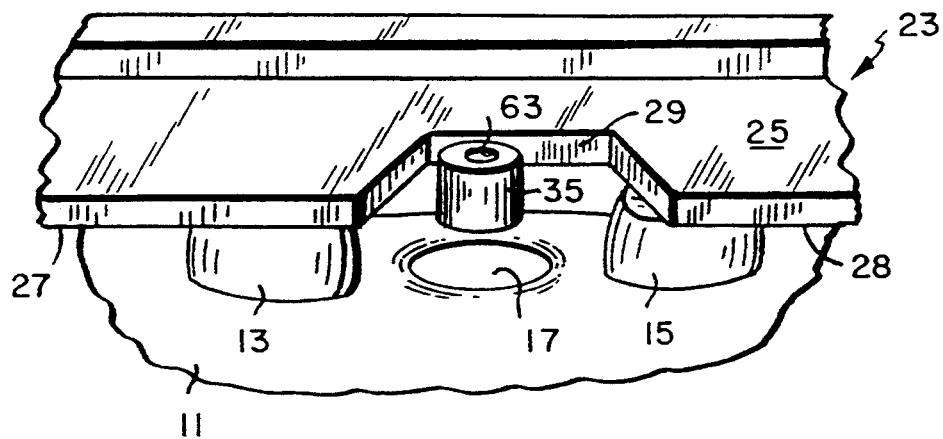

Turning now to FIG. 5, FIG. 5 represents the initial cast 73 of the surface features of the patient's mouth. Stent 23 is fitted to analogous surface feature of the cast. Thus, receiving surfaces 27 and 28 of the stent 23 are received on analogous features for the first molar 13 and the second molar 15. Screw 37 or screw 37' is removed from opening 63 of the index assembly 31 or 31'. A drill bit (not shown) is inserted through the opening 63 of index coping 35 to drill a pilot opening in the cast 73. The pilot opening (not shown) is expanded to a diameter and depth which will readily receive an implant analog 19'. The implant analog 19' corresponds in shape, size and threads, to the implant 19 now in the patient's mouth.

Figure 6:
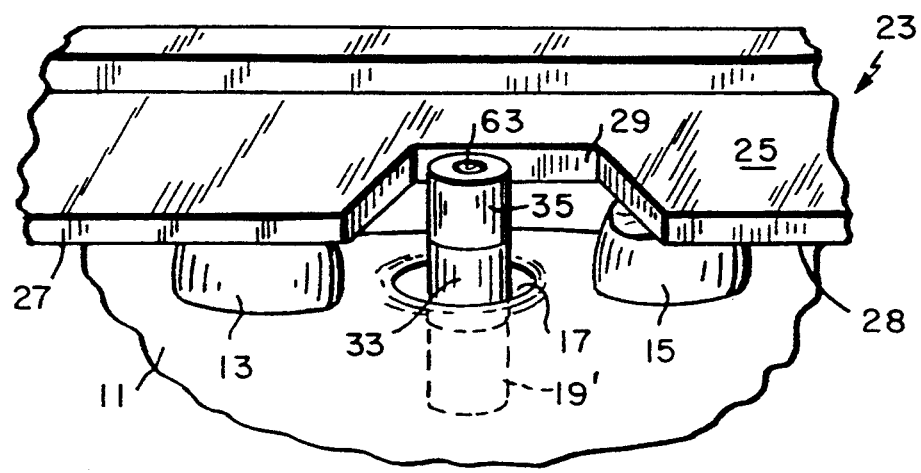

Turning now to FIG. 6, the stent 23 is removed from the surface features of the cast 73 and index assembly 31 or 31', and an implant analog 19' are assembled to the stent 23, as such like parts were assembled in the patient's mouth. The stent 23 with the index assembly 31 or 31' and the implant analog 19' are repositioned on the cast 73 and the implant analog 19' is fixed in place. Securing the implant analog 19' in the cast 73 while it is assembled to the index assembly 31 or 31' and stent 23, transfers to the cast the positional relationship, with respect to both horizontal and vertical axes and rotational relationship with respect to the threads, to the surface features.

The oral surgeon, restorative dentist, and dental laboratory, having a cast depicting an implant analog 19', with spatial orientation to the surface features identical to the implant 19 in the patient's mouth, can confidently select abutments and begin building a tooth prosthesis.

Figure 7:
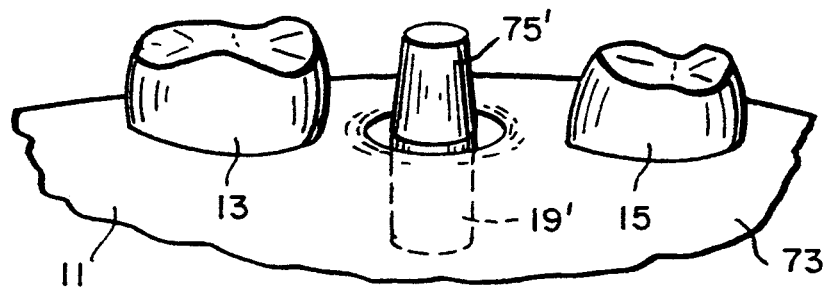
Figure 8:
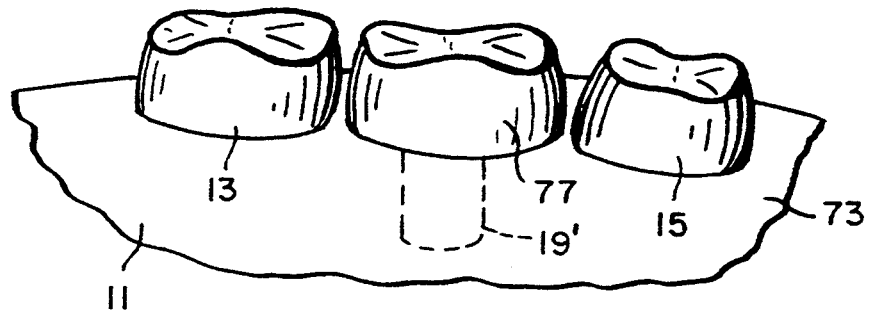

FIG. 7 illustrates an abutment analog 75' placed on the implant analog 19' in cast 73. FIG. 8 illustrates a tooth prosthesis 77 mounted on implant analog 19' and abutment analog 75'. The tooth prosthesis has the spatial relationship with respect to surface feature analogs as it will to actual surface features 19 in the patient's mouth.

The index assembly 31 affixed to the stent 23 is no longer needed to position an implant analog 19' in a cast. The index assembly 31 can be used to locate the position of implants 19 in the patient's mouth. The opening 63 of the index coping 35 is used to guide markers (not shown) such as screw 37 dipped or coated with ink.

In the alternative, index assembly 31, including the index coping 35, can be removed from the stent 23 to allow the stent to be used for purposes of removing tissue from above the implant 19 in the patient's mouth.

Figure 17A:
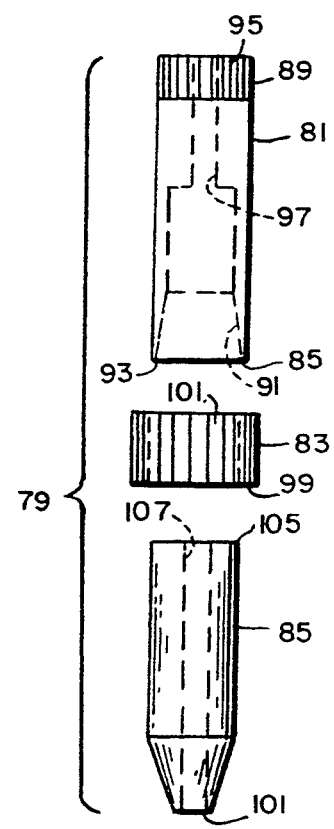
FIG. 17a depicts a tissue punch in cross-sectional view with supporting assembly.

Turning now to FIG. 17a, a tissue punch assembly 79 is comprised of the following components: a tissue punch 81, a tissue punch guide 83 and a tissue punch guide setter 85. The tissue punch assembly 79 is made of stainless steel.

Tissue punch 81 has a cylindrical shape having an outer diameter, an apical end 85 and an occlusal end 89. The apical end of the tissue punch has an opening 91. Edge 93 of opening 91 defines a cutting edge. Opening 91 defines a cavity adapted to receive tissue cut by edge 93 as the tissue punch 81 is compelled through tissue.

The occlusal end 89 of the tissue punch 81 includes a keyed opening 95 adapted to fit cooperating keyed extensions on handling equipment (not shown). A hole 97 extends through the tissue punch to allow the tissue punch to be secured to such handling equipment (not shown). The keyed opening 95 allows handling equipment to impart rotational movement to the tissue punch 81.

Figure 17B:
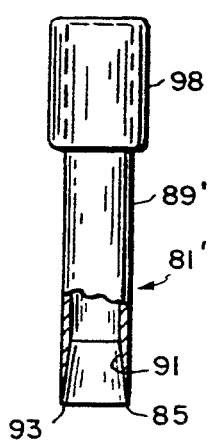
FIG. 17b depicts a partial cross-sectional view of a tissue punch embodying features of the present invention.
Figure 18:
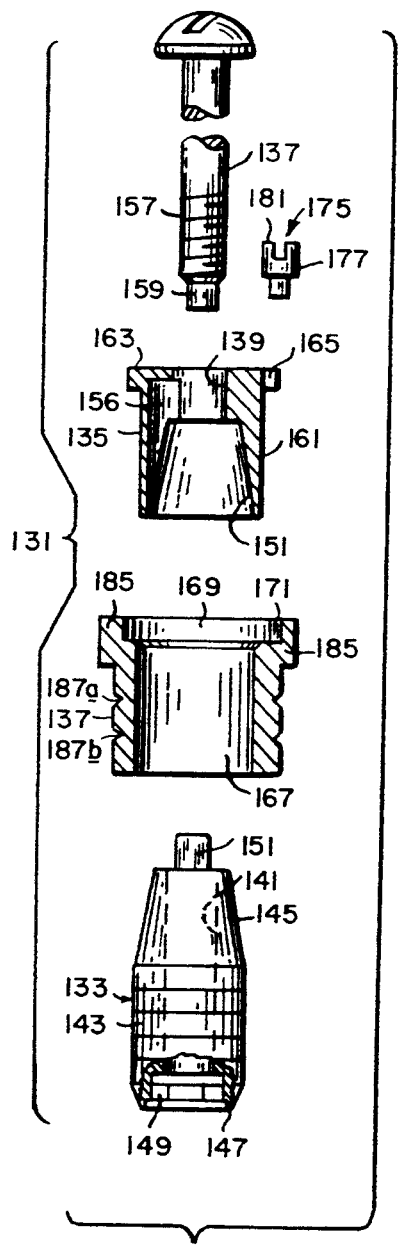
FIG. 18 depicts an indexing assembly capable of use with a stent, embodying features of the present invention.
Figure 19:
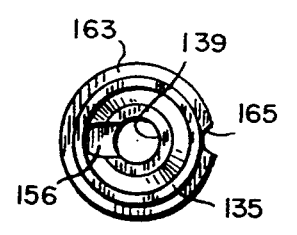
FIGS. 19-21 depict apical surfaces of components embodying features of the present invention.
Figure 20:
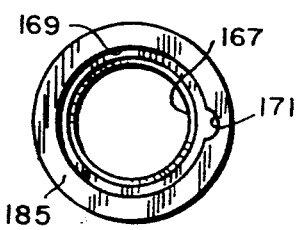

An alternate tissue punch 81' is illustrated in FIG. 17b. The apical features of the tissue punch are identical to the tissue punch previously described. The occlusal end 89' of the tissue punch 81' is elongated and is equipped with a handle 98, such as a rubber coating to facilitate manual operation.

Returning now to FIG. 17a, the tissue punch guide 83 is a cylindrical sleeve having an inner diameter, an apical end 99 and an occlusal end 101. The outer walls of the tissue punch guide 83 are provided with ribbing (not shown) to allow adhesion of the occlusal end 101 to the stent 23. The inner diameter of the tissue punch guide 83 is adapted to slidably receive tissue punch 81 and tissue punch guide 83.

The tissue punch guide setter 85 has a cylindrical shape and an apical end 103 and an occlusal end 105. The cylindrical shape has dimensions of length and outer diameter. The tissue punch guide setter 85 is capable of extending from the spanning section 29 to implant analog 19'. The diameter is sized to be received in tissue punch guide 83. The apical end 103 is tapered to allow the tissue punch guide setter 85 to be aligned on an implant analog 19'.

Tissue punch guide setter 85 has an axial opening 107 extending radially therethrough adapted to receive a screw 37'. Screw 37' is capable of being received in opening 107 of tissue punch guide setter 85, and within the threaded opening 21' of implant analog 19'.

Figure 9:
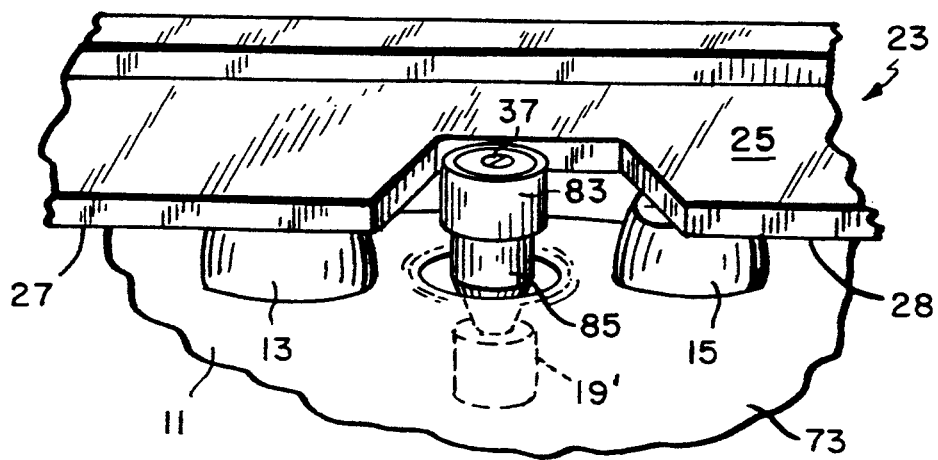

Turning now to FIG. 9, screw 37' secures tissue punch guide setter 85 to implant analog 91'. Tissue punch guide 83 is fitted over the tissue punch guide setter 85. The tissue punch guide setter 85, with tissue punch guide 83, is secured to implant analog 19' in cast 73 in a manner analogous to index assembly 31. The receiving surface 26 and 27 of stent 23 fit the surface features of the cast 73 analogous to first and second molars 13 and 15.

Tissue punch guide 83 is glued to spanning section 29 of stent 23 by suitable means such as acrylic adhesive. After the acrylic adhesive has cured, screw 37' can be removed from the tissue punch guide setter 85 and implant analog 19'. The tissue punch guide setter 85 is removed from the tissue punch guide 83. The tissue punch guide 83 retains the alignment and orientation with respect to the implant analog 19'.

After a four to six month period to allow the implant 19 to be received in the bone, the patient visits the oral surgeon for the second time. During the four to six month period, the soft tissue above the implant has healed and obscured the position of the implant 19.

Figure 10:
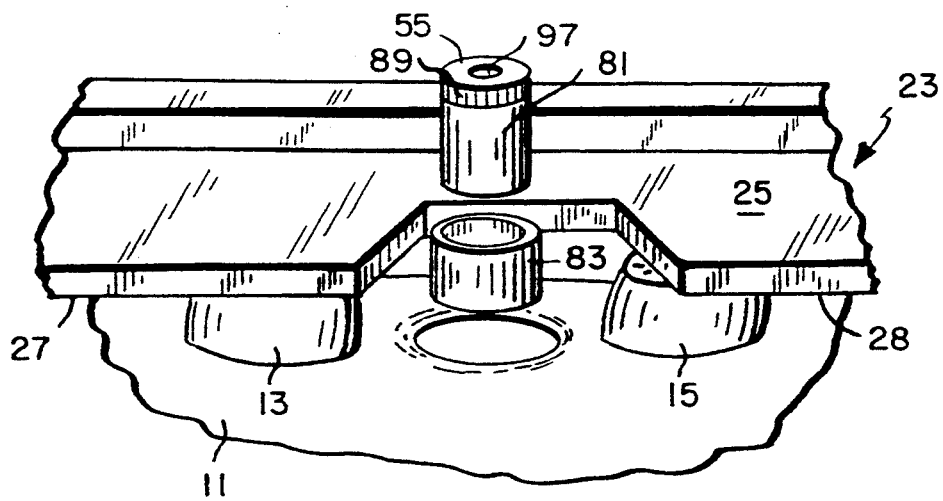

Turning now to FIG. 10, on the second visit of the patient to the oral surgeon, the dentist is able to quickly identify and expose the implant 19. The restorative dentist fits the stent 23 to the first molar 13 and second molar 15 at the respective receiving surface 27 and 28 of the elongated member 25. The tissue punch guide 83 retains the alignment and orientation necessary to direct tissue punch 81 to the implant 19 which is obscured beneath the surface of the gum tissue.

The oral surgeon directs the tissue punch 81 or 81' through the tissue punch guide 83 and into the soft tissue of the gum. The soft tissue of the gum is cut by edge 93 of tissue punch 81 as the tissue punch is compelled through the tissue with a rotating action. The tissue punch 81 reaches the implant 19, and thereafter is withdrawn. Tissue removed by the tissue punch 81 is retained within the opening 91.

Figure 11:
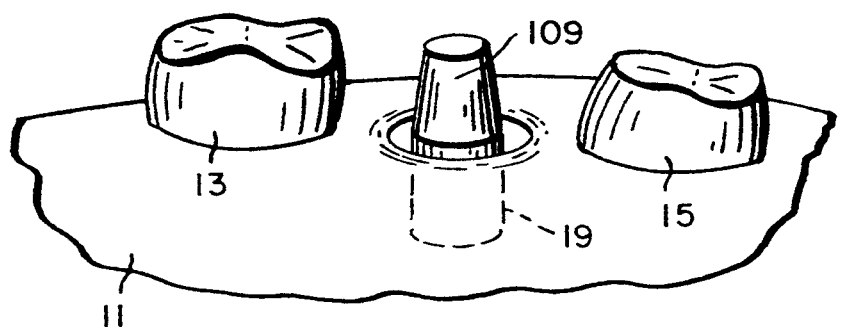

Having exposed the implant 19 the oral surgeon removes the stent 23 and can fit the implant 19 with a proper abutment 109, best illustrated in FIG. 11.

As a further aid to the oral surgeon, one embodiment of the present invention features an index assembly which incorporates features of a tissue punch guide and a tissue punch guide setter. Turning now to FIGS. 18–21, an index assembly, generally designated by the numeral 131 is depicted.

The index assembly is comprised of an implant coping 133, an index coping 135, a tissue punch guide 137, and screw 137. Screw 137 is capable of extending through cooperating openings 139 and 141 in the index coping 135 and implant coping 133. Screw 137 is adapted to be received in a threaded opening 21 of implant 19.

Implant coping 133 has an apical section 143 and an occlusal section 145. The apical section 143 has a cylindrical shape having a diameter and a circular apical surface 147. The diameter corresponds substantially to the cylindrical shape of the implant 19. The apical surface 147 has a keyed indentation 149 capable of receiving a keyed protrusion (not shown) on implant 19.

The occlusal section 145 extends from the apical section 143. The occlusal section 145 has a generally frustra conical shape altered with alignment tab 151. Alignment tab projects upward from the conical shape of the occlusal section 145. Alignment tab 151 allows the implant coping 133 to transfer the rotational position of the implant 19 to the index coping 135.

Figure 21:
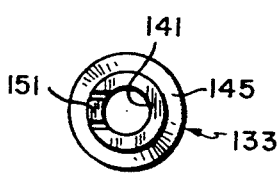

As seen in FIG. 21, the occlusal section 145 has an occlusal surface 153 which is generally circular in shape, which circle is interrupted by the alignment tab 151. Occlusal surface 153 has an opening 141 extending axially through the implant coping 131 to receive screw 137.

Returning now to FIG. 18, index coping 135 is adapted to receive the occlusal section 145 of implant coping 133 within cavity 155. An indentation 156 interrupts the cavity wall to allow cavity 155 to receive alignment tab 151 of the implant coping 133.

Opening 139 in index coping 135 cooperates with opening 141 in implant coping 133 to receive screw 137.

Screw 137 has a threaded section 157 capable of being received in threaded opening 21 of implant 19. To facilitate fitting screw 137 through the openings, screw 137 has a guide projection 159 extending from threaded section 157.

The index coping 133 has an outer cylindrical wall 161. An occlusal lip 163 extends radially outward from the occlusal edge of the index coping 133. The occlusal lip 161 has a first half circle notch 165 for alignment.

Index coping 133 is adapted to be received within tissue punch guide 137. Tissue punch guide 137 has a cylindrical cavity 167. Cylindrical cavity 167 has a rim 169 adapted to receive occlusal lip 163 of the index coping 133. Rim 169 has a second half circle notch 171. Nested within cavity 167, index coping is aligned with the first half circle notch 165 and second half circle notch 171 to make a complete circular hole, as can best be seen in FIGS. 19 and 20. First half circle notch 165 and second half circle notch 171 are adapted to receive pin 175. Returning not to FIG. 18, pin 175 has a head section 177 and peg section 179. Peg section 179 is cylindrical in shape, sized to be received within first half circle notch 165 and second half circle notch 171, rotationally immobilizing tissue punch guide 137 with respect to index coping 133. Peg section 179 and first half circle notch 165 and second half circle notch 171 may be threaded to secure tissue punch guide 137 to index coping 133 to form a single assemblage for ease in handling.

Head section 177 expands radially outward from peg section 179 to allow pin 175 to be more readily handled. A slot 181 in head section 177 allows pin 175 to be manipulated with a screw driver (not shown).

Tissue punch guide 137 is adapted to be affixed to a stent 23 by means of acrylic cement while retaining the index coping 133 in cavity 167. Thus, tissue punch guide forms part of the index assembly 131, and is set in position simultaneously with the index coping 133.

Tissue punch guide 137 has an outer cylindrical shape with a retention lip 185, and retention ridges 187a and 187b to receive glue and secure the index assembly 131 to a stent.

After an implant analog has been set in a cast, the index assembly 131 can be disassembled to allow tissue punch guide 137 to be used with a tissue punch, 81 or 81', as previously described.

Figure 22:
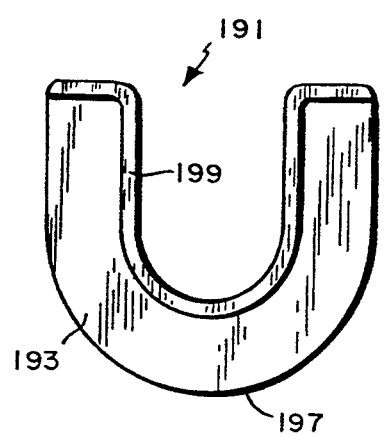
FIG. 22 depicts a top view of a registration tray embodying features of the present invention.

One embodiment of the present invention features a stent 23 which is substantially preformed. Turning now to FIG. 22, a registration tray, generally designated by the numeral 191 is illustrated. Registration tray 191 has a planar surface 193 having an inside edge 195 and an outside edge 197. The outside edge 197 is adapted to be positioned adjacent normal teeth positions in a patient's mouth. Thus, the registration tray 191 has a u-shaped appearance when viewed from occlusal or apical surfaces. The inside edge 195 is disposed lingually of the outside edge and defines an empty area for the patient's tongue. A supporting ridge 199 projects from the inside edge 195 to provide registration tray 191 with greater rigidity.

Preferably, registration tray 191 is made of clear material to allow an oral surgeon, restorative dentist and laboratory technician to see underlying features. Preferably, the material is a plastic acrylic capable of receiving acrylic cement to form surface feature receiving surfaces. A plastic material allows an oral surgeon or restorative dentist to remove the parts of the registration tray occlusal to the implant site about outer edge 197 to form a spanning section lingually disposed with respect to the implant size. The spanning section thus formed is adapted to receive index assemblies 31, 31' and 131.

Figure 12:
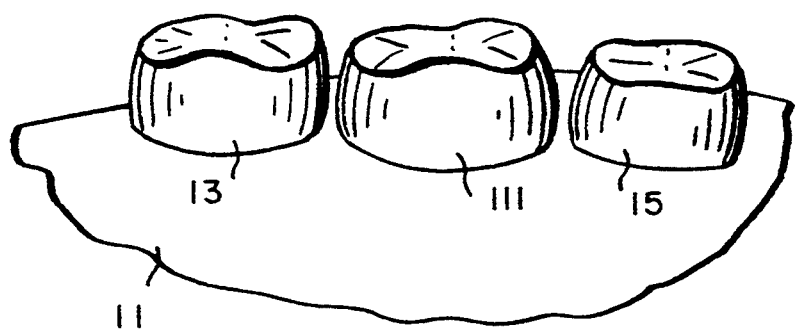

Having initiated construction of a tooth prosthesis prior to the second stage surgery, which tooth prosthesis corresponds to the spatial relationship of the implant and the surface features of the patient's mouth, the oral surgeon can make a first fit of a tooth prosthesis 111 to the abutment 109. The oral surgeon can fit a temporary tooth prosthesis as best illustrated in FIG. 12. The oral surgeon may refer the patient to a restorative dentist to complete the fitting of the tooth prosthesis.

The following example further exemplifies features of the present invention.

In 1982, a 62 year old male patient received a fixed partial denture in the right posterior mandible. The fixed partial denture replaced the missing lower right first and second premolars (FIGS. 1a and 1b). In 1989, a vertical fracture occurred in the mesial root of the first molar tooth necessitating extraction (FIG. 1c). The mesial root was surgically removed from beneath the fixed partial denture. In 1990, the fixed partial denture fractured through the solder connection between the pontics and a new fixed partial denture was considered. Due to the peridontially and mechanically weakened molar abutments and the long endentulous span, implants were selected to provide more predictable support for a new restoration in this quadrant.

Prior to the first stage surgery, kodachones, preliminary diagnostic casts, periapical radiographs, and a mandibular CT-scan were obtained. A diagnostic wax up of the teeth to be replaced by an implant supported restoration was fabricated on the diagnostic mandibular cast. From the diagnostic information, it was determined that two osseiontegrated implants would provide support for two fixed replacement teeth in this quadrant.

In order to register the location of the implants, two constitutive components of the positional index were prepared in the dental laboratory prior to first stage surgery; a resin surgical stent and a implant coping assembly. The implant coping assembly comprises an implant coping and an index coping.

The resin surgical stent was fabricated on the diagnostic cast using GC pattern resin. The resin surgical stent covered the lingual-occlusal surface of the teeth adjacent to the endentulous space. This lingual-occlusal seat allowed for intra-oral positioning of the stent on the adjacent dentition during first stage surgery. In the area of implant placement, the resin surgical stent was situated sufficiently to the lingual of the drilling sites to prevent interference with the implant coping assembly.

An index coping made by circumferentially applying pattern resin to a lubricated implant coping in the area of the facets. The circumferential application of pattern resin provided for the mechanical retention of the resin to the implant coping. The two facets on the surface of the implant coping registered the proper positional orientation for the transfer of the hexagon on the coronal aspect of the implant and prevented rotation of the circumferential resin ring. Lubrication of the implant coping allowed for easy removal and duplicable replacement of the implant coping in the circumferential resin ring. The circumferential ring of pattern resin forms the index coping placed on the impression coping did not interfere with the proper alignment of the impression coping retaining screw. The head of implant coping retaining screw was slotted to allow the use of a standard screw driver. Each implant coping and retaining screw was engraved with a number (FIG. 4C).

The remaining distal root of the mandibular first molar was extracted at the first stage surgical appointment in order to create additional access for implant placement. Two Branemark implants (III) were placed in the right mandibular premolar region. Both premolar implant fixtures were 13 mm in length and 3.75 mm in diameter. The CT-scan served to identify the mental foramen and the mandibular canal. Masticatory mucosa covered the right mandibular endentulous ridge segment. The masticatory mucosal tissue was quite thin and it measured 2 mm in depth. Both implants were placed uneventfully and were securely fixed to mandibular cortical bone.

After the placement of the implants was completed and their stability confirmed, an implant coping was secured to each implant with the corresponding retaining screw. The resin surgical stent was seated to place on the adjacent teeth and its position was just lingual to the modified implant coping. The index coping, of circumferentially applied pattern resin, was placed on each implant coping in close proximity to the resin surgical stent. The index coping assemblies were connected to the resin surgical stent through the index coping with Relate pattern resin and Super C liquid. In order to minimize the surgical time, Super C liquid was used because of its rapid setting capability. Once the copings were connected to the resin surgical stent, the retaining screws were unscrewed counterclockwise and the index coping/surgical stent complex was removed. Cover screws were then placed for each implant and surgical site closure was accomplished. The gingival tissue covering the implants was 2 mm in thickness.

The index coping/surgical stent complex was cold sterilized in Cidalent solution for 10 minutes. Since the implants were at a level slightly below the gingival tissue, an attempt to properly place the index coping/surgical stent complex on the diagnostic cast, in its index position on the adjacent teeth, set with interference from the stone on the endentulous ridge. Therefore, the implant copings were recovered from the two index coping attached to the surgical stent SSC. The surgical stent with the implant copings removed could then be seated back on the diagnostic cast without any interference. A straight handpiece 8 round bur was passively placed into the index coping and a pilot hole was made on the diagnostic cast. The direction of the bore for the hole in the stone was guided by the index coping mounted to the surgical stent seated on the diagnostic cast. Holes were then bored in the stone that were large enough to accomodate implant laboratory analogs.

The index coping/surgical stent complex was reassembled by replacing each engraved implant coping into its corresponding circumferential resin ring. Implant analogs were then secured to the index coping/surgical stent complex using the retaining screws. The entire assembly was then positioned passively back on the diagnostic cast.

Any stone interfering with a passive seat of the implant laboratory analogs in the bored holes was removed. Die stone was then vibrated around the analogs until the bored holes were filled and the implant laboratory analogs were surrounded. After the stone set the index coping/surgical stent complex was removed and the diagnostic cast then contained two implant analogs with an accurate transfer of the implant hex position. The diagnostic cast became a working cast for the initiation of laboratory restorative procedures.

The mandibular diagnostic cast had now been transformed into a working cast using two laboratory implant analogs which transferred the proper implant hex position from the oral cavity. Occlusal registration for the mandibular working cast and articulation with the maxillary cast had been determined during the diagnostic phase. The laboratory now had sufficient data to fabricate a provisional restoration, the fixed partial denture and an implant locating stent prior to second stage surgery.

Two implant temporary cylinders were positioned on the working cast and the cylinder height was shortened to a level dictated by the occlusion. A wax-up of the provisional restoration was performed on the two implant temporary laboratory cylinders and the acrylic was processed using the lost wax technique. Acrylic was removed 2-3 mm from the implant margin of the restoration and occlusal screw access holes allowed for screw retention of the provisional restoration (FIGS. 10a and 10b). The provisional restoration was ready for delivery at second stage surgery.

A framework wax-up was fabricated on the working cast using castable plastic components of the UCLA-type design. The apical end of the UCLA-type component, which fits onto the external hexagonal at the coronal aspect of the implant, is available either with an internal hexagonal or a circular surface. The external hexagonal on the coronal aspect of an implant is non-rotational when it engages the internal hexagonal of a single tooth restoration. A fixed partial denture supported by multiple implants (in this case two implants) is non-rotational if the implants are splinted together. Circular design castable plastic cylinders were used to insure complete seating of the ceramic gold framework onto the external hexagonal of the implants.

The framework, designed for a post ceramic solder connection, was cst in Deva IV ceramic gold alloy and the Vita porcelain was applied according to the color prescription determined at a pre-surgical appointment.

The working cast provided an accurate analog of intra-oral implant position. An implant locating stent was constructed to guide the surgeon at the time of second stage surgery.

In order to construct the implant locating stent, the surgical stent glued to the index coping was positioned on the working cast. Lubricated retaining screws without the corresponding implant copings were placed through the index coping on surgical stent screwed into the implant analogs on the working cast. Pattern resin was then filled into the index coping and forming an implant guide about the lubricated retaining screws. Once the pattern resin hardened, an access channel for the retaining screws was established within the index coping. The implant locating stent was formed on the working cast and held in place by the retaining screws. The implant locating stent was unscrewed from the working cast and the retaining screws could be moved freely in the access channels. At the time of second stage surgery, the apical tips of the retaining screws were to be inked with a surgical marker.

A circular tissue punch may be substituted for the inked apical tips for precisely locating and exposing the implants at the second stage surgery.

The patient was seen for second stage surgery three and one half months after initial implant placement. Soft tissue local infiltration anesthesia was administered. The implant locating stent was used to locate the position of the implants by inking the apical tips of the retaining screws with a surgical marker and seating the implant locating sting in place on the adjacent teeth. After removing the implant locating sting from the patient's mouth, an accurate location of the implants was obtained by the ink markings imprinted on the endentulous ridge. A circular incision was made around the ink markings and the implants were exposed without reflecting a surgical flap. The apical repositioning of buccal tissue was unnecessary due to the presence of sufficient masticatory mucosa. The accuracy of the technique was confirmed by replacing the implant locating sting back in position on the adjacent teeth and passively screwing the retaining screws into the implants.

As a continuation of the second stage procedure, the individual ceramic fixed partial denture restorations were tried in and secured to place with screws. Interproximal contact was adjusted and the seating of the fixed partial denture was confirmed with a radiograph. Occlusal contact in intercuspal position was adjusted using micro-req foil. A stone occlusal index was made to serve as a key for post ceramic soldering. The individual fixed partial denture units were removed and post ceramic soldering was accomplished in the dental laboratory.

The provisional restoration was also tried in as two separate units in order to insure a passive and accurate fit to the implants. The separate units were joined with autopolymerizing acrylic resin and the restoration was polished. The patient was discussed from the second stage surgical appointment with the provisional restoration secured in place with set screws.

One week following the second stage surgery, the patient returned for completion of restorative treatment. The provisional restoration was removed and the implant supported fixed partial denture secured in place with set screws. Proper seating of the restoration on the implants was again confirmed with a radiograph. The centtic occlusal contact was confirmed and lateral excursive movements were guided by the natural canine teeth. Screw access channels were filled with composite resin and the patient was dismissed. The patient was seen five weeks post insertion, in order to secure the tightness of the set screws.

Thus, the present inventions provide a final tooth prosthesis to the patient in a shorter period of time than was practical previously. Furthermore, the patient undergoes fewer visits to oral surgeons and restorative dentists. Such greater convenience, less discomfort, and reduction in overall cost is of great significance to patients and to the practice of dentistry. Patients have greater enthusiasm for prosthetic surgery.

The present inventions require less impression procedures than performed in the past. Abutment selections can be made earlier and with greater confidence. The present inventions reduce the need for temporary healing components and facilitates selection of temporary healing components for use at the second stage surgery.

The ability to preselect components and to fabricate prosthetics with an accurate mold of the patient's mouth, improves the probability that prosthetics will correspond with the features of the patient's mouth. Indeed, the present inventions, facilitates locating implants and can be used to guide initial fixture placement.

Dental laboratories having the time between stage 1 and stage 2 surgeries can devote additional time to the prosthetic to insure quality and fit.

While preferred embodiments have been illustrated and described, it is understood that the present invention is capable of variation and modification and, therefore, should not be limited to the precise details set forth but should include such changes and alterations that fall within the purview of the following claims.

I claim:

1. An indexing device for recording the position of a dental implant, having an implant coping releasably secured thereto, with respect to a stent releasably mounted to surface features and having a spanning section adjacent said implant, which implant coping has an apical section towards said implant and an occlusal section extending from said apical section, said occlusal section having alignment surfaces which relate to the rotational position of the implant coping and said implant, said indexing device comprising:

an index coping having a cavity, said cavity having a receiving alignment surface for receiving said alignment surface of said implant coping, said index coping having means for releasably receiving and securing said occlusal section of said implant coping and having means for securing and fixing said index coping to said spanning section of said stent; said index coping upon release from said implant coping and upon the release of said stent from surface features, recording the position relationship on the vertical and horizontal axis and the rotational relationship of said implant coping secured to said implant, said stent with said index coping secured thereto for receiving an implant coping analog for placing an implant analog in a cast and for identifying the position of said implant following removal of said implant coping and healing over the implant, said means for securing and fixing said index coping to said spanning section of said stent comprising a tissue punch guide, said tissue punch guide having a cylindrical cavity for receiving and securing said index coping within said cylindrical cavity, said cavity and index coping having cooperating alignment notches to secure said index coping and tissue punch guide in rotational alignment with said implant coping and implant, said tissue punch guide having stent receiving surfaces for securing said tissue punch guide to said stent to record the position of said implant, said tissue punch guide, upon release of said index coping, for receiving a cooperating interfitting tissue punch.

2. The indexing device of claim 1 further comprising a tissue punch, said tissue punch having a cylindrical housing having an outer diameter, an apical end and an occlusal end, said apical end having an opening having a knife edge, said opening defining a cavity for receiving tissue, said outer diameter of said cylindrical housing slideably received in said tissue punch guide upon removal of said index coping, to allow said tissue punch guide to direct said tissue punch to said implant upon placing said stent on said surface features.

3. A method of recording the position of a dental implant secured to a bone in an area having surface features, comprising the following steps:

a) releasably securing a stent to at least one surface feature, said stent comprising an elongated member having at least one receiving surface, and a spanning section; said receiving surface capable of receiving said surface feature, and permanently conforming thereto, to secure said stent to said surface feature, said spanning section adopted to extend adjacent said implant;

b) releasably securing indexing means to said dental implant, said indexing means for extending from said implant to said spanning section, said indexing means comprising an implant coping and an index coping, said implant coping adapted to be mounted to said implant, said implant coping having an apical section and an occlusal section, said apical section having a cylindrical shape having one end with a circular surface capable of being received on said implant, said occlusal section extending from said apical section and capable of releasably receiving said index coping, said index coping capable of releasably receiving said occlusal section of said implant coping and capable of being secured to said spanning section of said stent, said step comprising mounting said implant coping to said implant;

c) securing said indexing means to said spanning section; by securing said index coping to said spanning section as said implant coping is received in said index coping, to record the position of said implant with respect to said surface feature in the position of the index coping secured to the stent; and d) releasing said stent from said surface feature and said indexing means from said implant, by releasing said implant coping from said index coping to record the position of said implant with respect to said surface feature, in the position of the index coping secured to the stent.

4. The method of claim 3 comprising the step of securing said implant coping to said implant by screw means.

5. The method of claim 4 wherein said screw means comprise a screw section extending from said circular surface capable of being received by a cooperating threaded opening in said implant.

6. The method of claim 5 wherein said implant coping has a threaded opening capable of cooperating with screw means to secure said index coping to said implant coping.

7. The method of claim 4 wherein said implant coping and said index coping have cooperating openings capable of receiving a screw means which screw means is capable of being received in a cooperating threaded opening in said implant.

8. The method of claim 3 further comprising the step of making a cast of said surface features, said stent releasibly securing to said cast by surface receiving means to allow the position of said implant to be recorded in said cast.

9. The method of claim 8 comprising the step of securing said implant coping and an implant analog to said index coping, positioning said implant analog in the cast as said stent is secured to said surface features, to set the position of the implant analog in the cast in an analogous position with respect to surface features as the implant in said patient's mouth.

10. A method of exposing a dental implant secured to a bone in an area having surface features, comprising the following steps:
(a) securing a stent to at least one surface feature, said stent comprising an elongated member having a spanning section, at least one receiving surface corresponding to said surface feature to which said stent is secured, said spanning section extending adjacent said implant and having a tissue punch guide, said tissue punch guide having a guide surface adapted to receive a tissue punch and guide said tissue punch apically to said implant,
(b) fitting a tissue punch to said guide surfaces and directing said tissue punch to said implant, said tissue punch capable of cutting and removing tissue to expose said implant.

11. The method of claim 10 further comprising the following steps:
(a) securing guide setting means to said implant, said guide setting means capable of engaging said tissue punch guide in an alignment position; and
(b) fastening said tissue punch guide to said stent in an alignment position, to allow said tissue punch guide to direct said tissue punch to said implant.

* * * * *